(12) United States Patent
Mohapatra et al.

(10) Patent No.: US 10,093,622 B2
(45) Date of Patent: Oct. 9, 2018

(54) EFFICIENT PROCESS FOR THE SYNTHESIS OF CYCLIC AMIDES

(71) Applicant: ANTHEA AROMATICS PRIVATE LIMITED, Navi Mumbai (IN)

(72) Inventors: Manoj Kumar Mohapatra, Navi Mumbai (IN); Ramamohanrao Bendapudi, Navi Mumbai (IN); Paul Vincent Menacherry, Mumbai (IN); Vincent Paul, Mumbai (MH)

(73) Assignee: ANTHEA AROMATICS PRIVATE LIMITED, Navi Mumbai (IN)

( * ) Notice: Subject to any disclaimer, the term of this patent is extended or adjusted under 35 U.S.C. 154(b) by 0 days.

(21) Appl. No.: 15/562,518

(22) PCT Filed: Jun. 4, 2015

(86) PCT No.: PCT/IB2015/054222
§ 371 (c)(1),
(2) Date: Sep. 28, 2017

(87) PCT Pub. No.: WO2016/156932
PCT Pub. Date: Oct. 6, 2016

(65) Prior Publication Data
US 2018/0093949 A1   Apr. 5, 2018

(30) Foreign Application Priority Data
Apr. 2, 2015   (IN) .......................... 1410/MUM/2015

(51) Int. Cl.

| | | |
|---|---|---|
| *C07D 201/04* | (2006.01) | |
| *C07D 201/06* | (2006.01) | |
| *C01B 21/14* | (2006.01) | |
| *C01G 9/02* | (2006.01) | |
| *C07D 201/16* | (2006.01) | |
| *C07D 227/087* | (2006.01) | |
| *B01D 3/36* | (2006.01) | |

(52) U.S. Cl.
CPC ............ *C07D 201/06* (2013.01); *C01B 21/14* (2013.01); *C01G 9/02* (2013.01); *C07D 201/04* (2013.01); *C07D 201/16* (2013.01); *C07D 227/087* (2013.01); *B01D 3/36* (2013.01)

(58) Field of Classification Search
CPC ............................. C07D 201/04; C07D 201/06
See application file for complete search history.

(56) References Cited

U.S. PATENT DOCUMENTS

| | | | |
|---|---|---|---|
| 2,988,546 A | 6/1961 | Lippincott et al. | |
| 4,054,562 A | 10/1977 | Furkert | |
| 6,649,747 B1 | 11/2003 | Lohse | |
| 8,309,714 B2 * | 11/2012 | Kugimoto | ............ C07D 201/04 540/464 |

FOREIGN PATENT DOCUMENTS

| | | |
|---|---|---|
| EP | 2275407 | 1/2011 |
| JP | 2001019670 | 1/2001 |
| WO | 2009153470 | 12/2009 |

OTHER PUBLICATIONS

Alain Laurent et al. "Fast Synthesis of Amino Acid Salts and Lactams without Solvent under Microwave Irradiation" J. Chem. Soc., Chem. Commun., 1995.
Lin-Fei Xiao, "p-Toluenesulfonic acid mediated zinc chloride: highly effective catalyst for the Beckmann rearrangement", Tetrahedron Letters 48 (2007) 7218-7221, 2007 Elsevier Ltd.
Hashem Sharaghi et al. "Solvent-Fre One-Step Beckmann Rearrangement of Ketones and Aldehydes by Zinc Oxide" Synthesis 2002, No. 8, 04 06 2002.
International Search Report and Written Opinion dated Sep. 14. 2015 for PCT/IB2015/054222.

* cited by examiner

*Primary Examiner* — Bruck Kifle

(57) ABSTRACT

Disclosed herein is an efficient, economical, industrially advantageous, straight-through process for the preparation of cyclic amides, also referred as lactams, in substantially pure form and high yield, from the corresponding cyclic ketones and a hydroxylammonium salt, using a combination of amphoteric metal oxide or amphoteric masked metal oxide and a base.

10 Claims, No Drawings

EFFICIENT PROCESS FOR THE SYNTHESIS OF CYCLIC AMIDES

FIELD OF TECHNOLOGY

Disclosed herein is an efficient, economical, industrially advantageous, straight-through process for the synthesis of cyclic amides, also referred as lactams, in substantially pure form and high yield, from the corresponding cyclic ketones and a hydroxyl ammonium salt, using a combination of amphoteric metal oxide or amphoteric masked metal oxide and a base.

Herein straight-through chemical process is defined as a sequence of reactions which are carried out in-situ, with minimum use of solvents, and which does not require isolation and/or purification at intermediate stages, to give the desired product in substantially pure form and high yield.

The present invention relates to a process for producing cyclic amides also referred as lactams. Lactams are a class of compounds useful as raw materials and/or intermediates for pharmaceuticals, agrochemicals, dyes and polyamides. A major use of lactam is as monomer in the manufacture of polyamides. The process of the present invention relates to a straight-through process for producing a cyclic amide/lactam wherein a higher-quality amide compound is produced without generating byproducts by the in-situ rearrangement reaction of an oxime formed from the corresponding ketone.

The present invention relates to a process for the preparation of cyclic amides/lactams of Formula (I) obtained from the corresponding compound of Formula II.

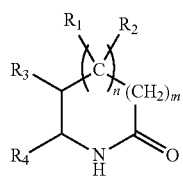

Formula I

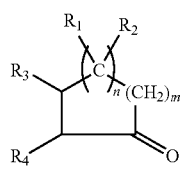

Formula II wherein n and m each are independently selected from 0, 1, 2, 3, 4, 5, 6, 7, 8 or 9 and the sum of n+m is at least 2, and the compounds of Formula I and II have substituents $R_1$, $R_2$, $R_3$ and $R_4$,
where $R_1$, $R_2$, R3 and $R_4$ are independently selected from hydrogen, alkyl, alkenyl, alkynyl, cycloalkyl, cyclo alkenyl, aryl, aralkyl and aromatic or non aromatic heterocycle, or R1, R2, R3 and R4 can be combined together to form a substituted or unsubstituted cycloalkyl or cycloaryl moiety, including bicyclic or heterocyclic moieties.

When $R_1$, $R_2$, $R_3$ and $R_4$ are H, n is 1 and m is 8 (sum of n and m is 9), then the compound of Formula I represents laurolactam, which is represented by compound of Formula III and the said lactam is particularly useful as a monomer for polyamides which exhibit excellent flexibility, water resistance and solvent resistance and is a key raw material for Nylon-12. The said compound of Formula III is prepared by using cyclododecanone of Formula IV as a starting material.

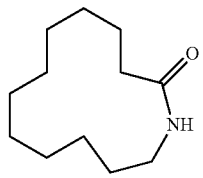

Formula III

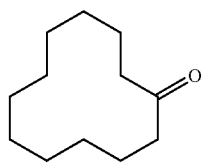

Formula IV

The process disclosed herein requires minimum use of solvents, and does not require isolation/purification at intermediate stage, thereby minimizing unit operations and handling losses during plant-scale operations. Furthermore, under these simplified process conditions the product is obtained in high yields and with high purity.

The inventive method is characterized by the fact that the cyclic ketone of Formula II is contacted with hydroxylammonium salt in presence of an amphoteric metal oxide or amphoteric masked metal oxide and a base, resulting in the formation of an oxime as an intermediate (which does not require isolation and/or purification) with simultaneous formation of the corresponding metal salt as a byproduct, which further catalyses the Beckmann rearrangement of the oxime into the corresponding cyclic amide/lactam of Formula I in the subsequent in-situ reaction step of the chemical process. The salient feature of the invention is the use of a amphoteric metal oxide or amphoteric masked metal oxide in combination with a base, which not only increases the yield in the transformation to the oxime intermediate, but also the amphoteric metal oxide or amphoteric masked metal oxide is in-situ gets converted into the corresponding metal salt which catalyses the subsequent step of the synthesis to form the lactam, the so called rearrangement reaction.

Particularly, the present invention relates to a process for making laurolactam of Formula III, useful as a starting material for Nylon-12, by Beckmann rearrangement of cyclododecanone oxime formed in-situ by contacting cyclododecanone of Formula IV with hydroxyl amine hydrochloride, using a combination of amphoteric metal oxide or amphoteric masked metal oxide and a base.

The inventive method is best understood by considering the general schematic presentation as shown herein below:

i) Hydroxyl ammonium salt
ii) amphoteric metal oxide of amphoteric metal masked oxide Ketone
Formula I
→ Oxime formation step iii) Catalyst (metal salt formed during oxime reaction)
iv) Rearrangement solvent Oxime → Rearrangement step → Cyclic amide
Formula II The inventive method is further illustrated by considering preparation of laurolactam as a specific example as given herein below:

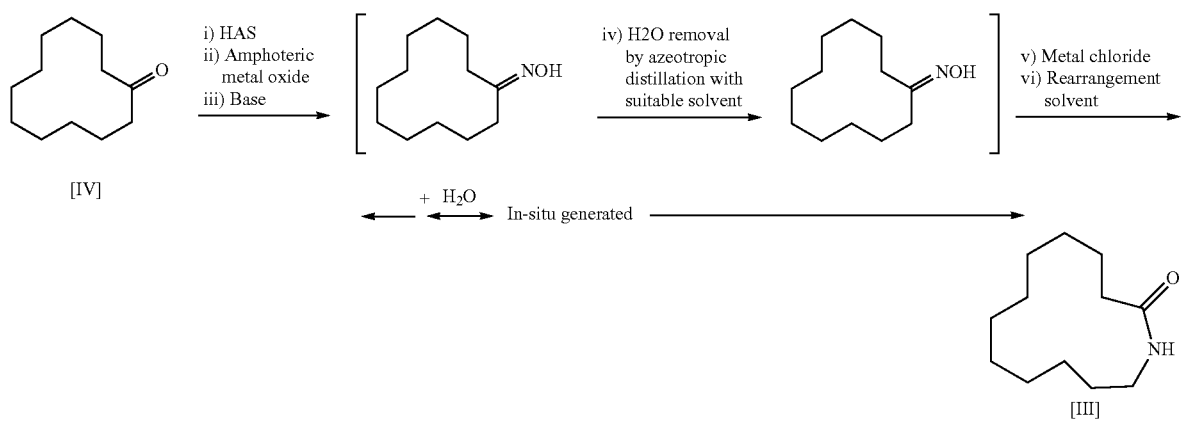

Where i) HAS (hydroxylammonium salt) is hydroxylamine hydrochloride
ii) Amphoteric metal oxide is zinc oxide
ii) Base is Sodium Carbonate
iv) Suitable solvent for azeotropic distillation is toluene
v) Metal chloride is zinc chloride formed as by-product
vi) Rearrangement solvent is acetonitrile Water is formed as a by-product during the formation of oxime intermediate which requires to be removed to facilitate Beckmann rearrangement reaction. This is easily achieved by azeotropic distillation using an appropriate solvent, before the said rearrangement proceeds.

BACKGROUND OF THE INVENTION

There are various chemical methods disclosed in the prior art for the synthesis of said cyclic amides also referred as lactams of Formula I.

J. Chem. Soc., Chem. Communication, 1995, 1101-1101 discloses the reaction of hydroxylamine-O-sulfonic acid with alicyclic ketones over SiO2 and no solvent under microwave irradiation to give an amino acid salt, which cyclises in high yield to the corresponding lactam after work up in basic medium.

WO/2009/153470 discloses a method for preparing lactams wherein photonitrosation of a cycloalkane is carried out using nitrosyl chloride (NOCl). According to the invention, said photonitrosation is carried out by means of LEDs emitting a monochromatic light. The method according to the invention also includes a step comprising Beckmann transposition/dechlorination of the oxime hydrochloride generated during said photonitrosation, preferably carried out in a glass micro reactor. The drawback associated with this method is the use of monochromatic light making it difficult to proceed on large scale and therefore limits commercialization of the process.

U.S. Pat. No. 4,054,562 discloses a process for manufacturing a lactam which includes rearranging a cycloalkanone-oxime with sulfuric acid to form the lactam, neutralizing the rearrangement mixture with ammonia to form ammonium sulfate, and separating the lactam and ammonium sulfate. The improvement comprises the recycling of the by-products which are generated during the reaction. However, a major drawback of this process is the high temperatures required, in the range 240°-1250° C. for the decomposition of ammonium sulfate to generate sulfuric acid and its subsequent reuse.

U.S. Pat. No. 2,988,546A discloses a process for the conversion of $C_{10}$ to $C_{18}$ cyclic ketones to the corresponding lactams wherein cyclic ketone is reacted with hydrazoic acid in the presence of a strong acid to obtain lactam, the hydrazoic acid being generated from an alkali azide such as sodium azide. The drawback associated with this method is the use of hazardous and unsafe alkali azide.

U.S. Pat. No. 8,309,714B2 discloses a process comprising reaction of cyclododecanone with hydroxylamine in an aqueous solution in the presence of an oxime formation solvent to produce cyclododecanone oxime, b) separating the reaction mixture obtained after the oxime-forming step into an oil and an aqueous phases and collecting a solution of cyclododecanone oxime in the oil phase; (c) removing a part or all of the oxime formation solvent and dissolved water from the solution of cyclododecanone oxime which is collected as an oil phase in the oil/aqueous phase separation step, whereby preparing a solution containing a solvent to be used in a rearrangement reaction in a later step and the cyclododecanone oxime; (d) producing laurolactam from cyclododecanone oxime by rearrangement reaction using an aromatic-ring containing compound as a rearrangement catalyst; and (e) separating and removing the solvent and the rearrangement catalyst from the reaction mixture after the rearrangement step, and purifying the laurolactam. A major drawback of this method is that it involves multiple unit operations as stated herein above.

JP2001019670A, 2001 Jan. 23 discloses a use of a catalyst comprising zeolite-ZnO mixture for rearrangement reaction. The zeolite skeleton is composed of at least silicon, zinc and oxygen and the ratio of Si/Zn in the zeolite skeleton is preferably 10-2,000. The catalyst is obtained by bringing a raw material of silicon oxide, a raw material of zinc oxide and a raw material of an alkali metal into contact with an organic base, such as tetraethylammonium cation, etc., to prepare a mixed solution and maintaining the mixed solution under a specific condition to form the zeolite-ZnO catalyst as a crystal. A Bamberger rearrangement, a Chapman rearrangement, etc., may be cited as the rearrangement reactions using the catalyst besides a Beckmann rearrangement reaction to produce an amide compound from the corresponding oxime compound.

Tetrahedron Letters, 48(40), 7218-7221 (2007) discloses the use of p-toluene sulphonic acid mediated zinc chloride as a very effective catalyst for liquid-phase Beckmann rearrangement of ketoximes in acetonitrile. Reported yield of cyclic amide from corresponding cyclododecanone oxime is 93%.

EP2275407 discloses a process for producing an amide or lactam, wherein catalytic amounts of an acidic chloride, such as thionyl chloride, and a Lewis acid are used in Beckmann rearrangement of an oxime compound. In accordance with the process, side reactions during Beckmann rearrangement can be so controlled that selectivity can be improved and discoloration of the product due to presence of impurities can be minimised, giving a high-quality amide or lactam.

Synthesis, 2002, 1057-1059 discloses solvent free and one step Beckmann rearrangement of ketones and aldehydes by using zinc oxide. It discloses the reaction of ketone or aldehyde with hydroxylamine hydrochloride and ZnO, wherein the reagents were mixed thoroughly and the mixture was heated in an oil bath at 140-170° C. without using any other additional solvent. In case of when cyclohexanone or cycloheptanone reacts with hydroxyl amine hydrochloride in presence of zinc oxide at temperature of 140-170° the reported yields of the corresponding cyclic amides (lactam) are 85% and 83% respectively. In this case the ZnO is used in excess of stoichiometric quantity.

Furthermore, it is known from U.S. Pat. No. 6,649,747 that during the production of laurolactam comprising converting cyclododecanone to an oxime and subjecting the said cyclododecanone oxime to the Beckmann rearrangement reaction, if the temperature of the Beckmann rearrangement reaction is too high, the cyclododecanone oxime gets decomposed, and the resultant laurolactam is unsatisfactory due to the low quality thereof Therefore, it is seen that the technical problem associated with the prior art include,
1. Use of multiple solvents and isolation/purification at intermediate stages, thereby increasing the unit operations and resulting into the reduced yield and increased cost of the process.
2. Decomposition of oxime at high temperature.
3. Formation of impurities during the Beckmann rearrangement reaction due to high temperature and high acidity, resulting in low yields.
4. Discoloration of the product due to impurity formation during the Beckmann rearrangement stage.

The processes disclosed in the prior art and described hereinabove suffer from various drawbacks such as need for multiple unit operations like solvent recovery and/or isolation/purification at intermediate stage, lower yield and poor quality of product, or are otherwise unsuitable for large-scale industrial production. This necessitates the development of an improved process for the preparation of cyclic amides of Formula I, also referred to as lactams, which minimizes the use of solvents and the number of unit operations, provides better yield and higher purity of product and is suitable for large-scale industrial scale manufacture.

Although the method reported in Synthesis, 2002, 1057-1059 discloses solvent free and one step Beckmann rearrangement of ketones and aldehydes by using zinc oxide, it has been found that lactam formed undergoes the polymerization resulting into low yield and low purity with polymer as an impurity.

The inventors of the present invention based on their expertise and experiments revealed that when hydroxylammonium salt reacts with the amphoteric metal oxide or amphoteric masked metal oxide to produce the corresponding metal salt, the presence of metal salt in excess can reduce the purity and yield of the final product in the subsequent rearrangement reaction, as understood from the example illustrated herein below.

For example, when zinc oxide reacts with hydroxyl amine hydrochloride, it produces water and zinc chloride.

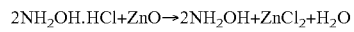

It has been observed by the inventors of the present invention that excess amount of $ZnCl_2$ causes the polymerization of the lactam so produced during the reaction at later stage. Therefore, it is essential to control the amount of metal salt present in the reaction medium to avoid polymerization of said lactam and isolate high purity cyclic lactam in high yield.

The inventors of the present invention have addressed the issue by providing a solution comprising use of a base in combination with the amphoteric metal oxide or amphoteric masked metal oxide, which results in increased yield and the purity of the cyclic amide formed.

There has not been any teaching or motivation in the prior art which can address the shortcomings in the prior art for preparing cyclic amides of Formula I comprising using amphoteric metal oxide or amphoteric masked metal oxide in combination with a base for the formation of corresponding oxime, and which after oxime formation provides a suitable reaction medium with desired level of corresponding metal salt for facilitating the subsequent in-situ rearrangement into corresponding lactam, without causing excess polymerization, comprising the use of amphoteric metal oxide or amphoteric masked metal oxide in less than stoichiometric quantities, the use of base to neutralize the remaining acid, and optionally leaving a small quantity of free acid to catalyze the subsequent reaction, whereby corresponding lactam is obtained in substantially high yield, and free of polymer impurity.

While working on the development of the present invention, the inventors observed that when cyclic ketone reacts with hydroxyl amine hydrochloride in presence of amphoteric metal oxide or amphoteric masked metal oxide in stoichiometric quantity it yielded only 61% of corresponding cyclic amide (w/w on cyclic ketone).

It was found that when the amphoteric metal oxide or amphoteric masked metal oxide was used in combination with a base, the yield of cyclic amide is significantly increased.

Furthermore, it was found that when the quantity of amphoteric metal oxide or amphoteric masked metal oxide in combination with base used resulted in complete neutralization of the acid component of the hydroxylammonium salt, the subsequent rearrangement reaction was sluggish, and that the presence of some acidity was required to facilitate the subsequent rearrangement reaction.

Furthermore, it was found that the required acidity is achieved by adjusting the quantity of amphoteric metal oxide or amphoteric masked metal oxide in combination with base used in the preparation of oxime to less than stoichiometric quantity required for complete neutralization of the acid component of the hydroxylammonium salt. Alternatively acidic material such as p-toluene sulfonic acid, is separately introduced after the oxime preparation to facilitate the subsequent rearrangement.

Furthermore, when no amphoteric metal oxide or amphoteric masked metal oxide is used and the reaction of cyclic ketone and hydroxyl amine salt is allowed to take place in presence of a base only, the obtained yield of corresponding amide was low, substantiating the observation of the inventors that it is advantageous to use the combination of amphoteric metal oxide or amphoteric masked metal oxide and a base in a suitable ratio to obtain high purity lactam in high yield and without formation of polymer.

The results are illustrated herein below in Table 1, for the preparation of laurolactam wherein zinc oxide represents the amphoteric metal oxide or amphoteric masked metal oxide and sodium carbonate represents the base.

TABLE 1

| Condition | Cyclododecanone (mol) | NH$_2$OH•HCl (mol) | ZnO (mol) | Na$_2$CO$_3$ (mol) | laurolactam Yield (w/w cyclododecanone) |
|---|---|---|---|---|---|
| Only ZnO used in reaction | 1.0 | 1.1 | — | 0.5 | 61% |
| Combination of ZnO and Na$_2$CO$_3$ used in reaction | 1.0 | 1.1 | 0.05 | 0.45 | 63.7% (additional ZnCl$_2$ was added in second stage to complete reaction) |
|  | 1.0 | 1.1 | 0.1 | 0.4 | 96.1 |
|  | 1.0 | 1.1 | 0.2 | 0.3 | 87.9% |
| Only Na$_2$CO$_3$ used in the reaction | 1.0 | 1.1 | — | 0.5 | 34% |

The present invention discloses a straight through process for manufacture of cyclic amides, also called as lactams, and provides an excellent process providing solution to the problems associated with the processes disclosed therein in the prior art for the preparation of cyclic amides of Formula I and the details are described herein after in the description.

The object of the present invention is to provide a solution to the technical problems associated with the processes disclosed therein the prior art for the preparation of cyclic amides of Formula I also referred as lactams. Keeping the said objective in view, the present invention provides an industrially viable and economical process thereby eliminating the above mentioned shortcomings associated with the processes disclosed in the prior art for the preparation of cyclic amides of Formula I.

OBJECT AND SUMMARY OF THE INVENTION

The inventors of the present invention disclose herein an efficient and selective process for the preparation of compound of Formula I from the corresponding cyclic ketone of Formula II comprising a sequence of reactions which are carried out in-situ, and which does not require isolation/purification at intermediate stage to give the desired product in substantially pure form and high yield.

The first aspect of the present invention is to provide an improved straight-through process for the preparation of cyclic amides, also referred as lactams, of Formula I from the compound of Formula II.

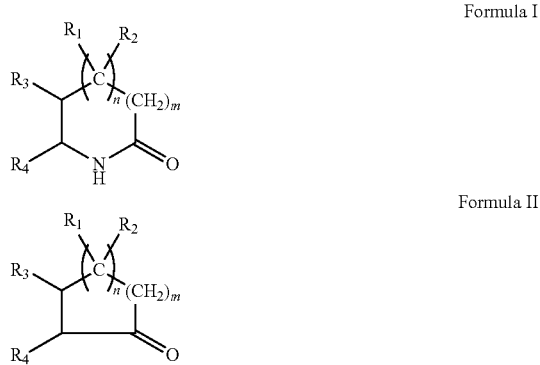

Formula I

Formula II wherein n and m each are independently selected from 0, 1, 2, 3, 4, 5, 6, 7, 8 or 9 and the sum of n+m is at least 2, and the compounds of Formula I and II have substituents R$_1$, R$_2$, R$_3$ and R$_4$, where R$_1$, R$_2$, R3 and R$_4$ are independently of and selected from hydrogen, alkyl, alkenyl, alkynyl, cycloalkyl, cyclo alkenyl, aryl, aralkyl and aromatic or non aromatic heterocycle, or R1, R2, R3 and R4 can be combined together to form a substituted or unsubstituted cycloalkyl or cycloaryl moiety, including bicyclic or heterocyclic moieties.

The second aspect of the present invention is to avoid isolation and purification of the intermediate stage thereby reducing the number of unit operations on plant scale, minimizing handling losses and increasing efficiency.

The third aspect of the present invention is to use amphoteric metal oxide or amphoteric masked metal oxide during the preparation of oxime which insitu generates the corresponding metal salt as a byproduct that catalyses the subsequent rearrangement reaction of oxime resulting into corresponding lactam.

The fourth aspect of the present invention is to use a base in combination with amphoteric metal oxide or amphoteric masked metal oxide which maintains the required level of acidity for the subsequent rearrangement reaction, and thereby avoids the polymerization of the lactam so formed during the reaction.

The fifth aspect of the present invention is to provide an improved, economical and industrially viable straight-through chemical process for the preparation of lactam of the Formula I in high yield of about 95%.

The sixth aspect of the invention is to provide an improved, economical and industrially viable straight-through chemical process for the preparation of lactam of the Formula I from ketone of Formula II having purity of about 99%.

The seventh aspect of the invention is to provide an improved, economical and industrially viable straight-through chemical process for the preparation of laurolactam of the Formula III from cyclododecanone of Formula IV having the yield of about 95% and purity of more than 99%.

Advantages Over the Prior Art

The process disclosed herein has the following distinct advantages over the prior art:
i) A straight-through chemical process for the preparation of compound of Formula I in substantially pure form and high yield, from the corresponding ketone of Formula II, without isolation and purification at intermediate stages, thereby making the process more economical and industrially viable, and wherein the product is obtained in good yield and in substantially pure form.

ii) A straight through chemical process for the preparation of laurolactam having more than about 99% purity in about 95% yield using cyclododecanone as a starting material.

SUMMARY OF THE INVENTION

Disclosed herein is an efficient, economical, industrially advantageous, straight-through process for the preparation of cyclic amides of Formula I, also referred as lactams, in substantially pure form and high yield, from the corresponding cyclic ketones.

Herein straight-through chemical process is defined as a sequence of reactions which are carried out in-situ without isolation/purification at intermediate stages, to give the desired product in substantially pure form and high yield.

The present invention relates to a process for the preparation of cyclic amides, also referred as lactams, of Formula (I) obtained from the corresponding compound of Formula II.

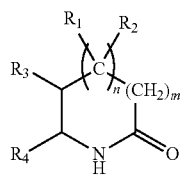

Formula I

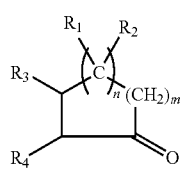

Formula II wherein n and m each are independently selected from 0, 1, 2, 3, 4, 5, 6, 7, 8 or 9 and the sum of n+m is at least 2, and the compounds of Formula I and II have substituents $R_1$, $R_2$, $R_3$ and $R_4$, where $R_1$, $R_2$, $R3$ and $R_4$ are independently of and selected from hydrogen, alkyl, alkenyl, alkynyl, cycloalkyl, cyclo alkenyl, aryl, aralkyl and aromatic or non aromatic heterocycle, or R1, R2, R3 and R4 can be combined together to form a substituted or unsubstituted cycloalkyl or cycloaryl moiety, including bicyclic or heterocyclic moieties.

When $R_1$, $R_2$, $R_3$ and $R_4$ are H, n is 1 and m is 8, then the compound of Formula I represents laurolactam, key raw material for Nylon 12, which is represented by a compound of Formula III is particularly useful because it provides a polymer exhibiting excellent flexibility, water resistance and solvent resistance. The said compound of Formula III is prepared by using cyclododecanone of Formula IV as a starting material.

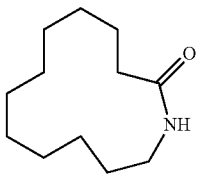

Formula III

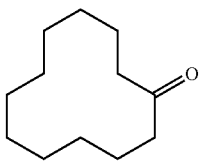

Formula IV

DETAILED DESCRIPTION

Unless otherwise specified all parts and percentages set forth herein are weight percentages. Unless otherwise stated as used herein the term "a" or "an" include one or more components also referred as reactants or materials or solvent. The present invention may comprise, consist of, or consist essentially of the reaction or processing steps set forth herein, unless otherwise stated.

Reference will now be made in detail to the preferred embodiments of the invention. This invention may, however, be embodied in many different forms and should not be construed as limited to the embodiments set forth herein. In addition, and as well be appreciated by one skilled in the art, the invention may be embodied as a method, system or process.

It is also to be understood that the technology disclosed herein is for the purpose of describing particular embodiments only, and is not intended to be limiting.

The term "about" means±10%.

The term "substantially pure" means purity greater than 95%.

The present invention relates to an industrially acceptable improved process for the preparation of lactam of Formula I. The present invention not only reduces process steps and minimizes unit operation but also minimizes yield loss by avoiding isolation and/or purification of intermediates, to manufacture lactam of Formula I in substantially pure form and in high yield.

In one embodiment disclosed herein is a straight-through chemical process for the preparation of compound of Formula I, wherein values of m and n and substituents $R_1$, $R_2$, $R_3$ and $R_4$ are same as described hereinabove;

and comprising:

contacting compound of Formula II with hydroxylammonium salt, amphoteric metal oxide or amphoteric masked metal oxide and a base with no solvent and the mixture is heated at about 85° C. for about one and half hours for the in-situ preparation of compound of Formula X,

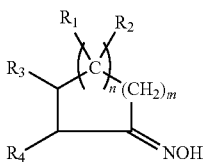

wherein n and m each are independently selected from 0, 1, 2, 3, 4, 5, 6, 7, 8 or 9 and the sum of n+m is at least 2, and the compounds of Formula I and II have substituents $R_1$, $R_2$, $R_3$ and $R_4$,

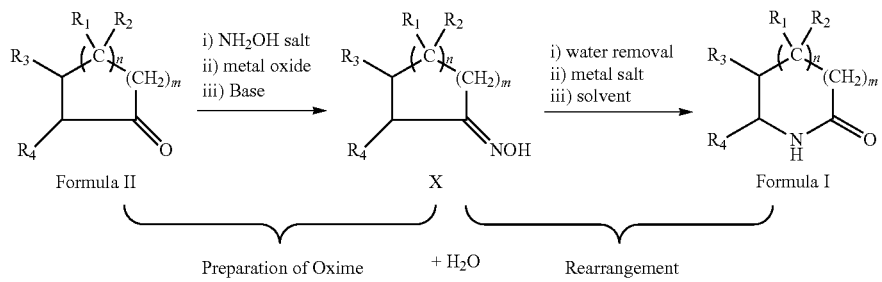

where $R_1$, $R_2$, R3 and $R_4$ are independently of and selected from hydrogen, alkyl, alkenyl, alkynyl, cycloalkyl, cyclo alkenyl, aryl, aralkyl and aromatic or non aromatic heterocycle, or
R1, R2, R3 and R4 can be combined together to form a substituted or unsubstituted cycloalkyl or cycloaryl moiety, including bicyclic or heterocyclic moieties.

The compound of Formula X is referred to as oxime; the reaction mass obtained hereinabove containing compound of Formula X as such without isolation and/or purification, is contacted with a suitable solvent capable to remove water that is formed during the reaction by azeotropic distillation. The said azeotropically dried oxime is then contacted with a suitable solvent, hereinafter referred to as rearrangement solvent, when the metal salt formed as a byproduct during the formation of the oxime, in the presence of required acidity, catalyses the rearrangement reaction resulting into the formation of corresponding compound of Formula I.

Herein the process for converting the in-situ formed compound of Formula X into corresponding lactam is referred as Beckmann rearrangement reaction.

Herein contacting means reacting, adding, refluxing, mixing, stirring and the like.

Herein hydroxylammonium salt is preferably hydroxyl amine hydrochloride.

Amphoteric metal oxides and amphoteric masked metal oxides comprises metal oxides, metal hydroxides, metal carbonates, metal bicarbonates and the likes of the metals such as zinc, aluminium, tin, lead, iron, cadmium and the likes.

The amphoteric metal oxide or amphoteric masked metal oxide is used singly or in mixtures thereof.

Preferably the amphoteric metal oxide or amphoteric metal masked oxide is zinc oxide.

The base is selected from the group comprising alkali metal hydroxides, alkali metal oxides, alkali metal carbonates, alkali metal bicarbonates and other the likes.

Preferably the base is sodium carbonate.

The reaction step of azeotropic drying described herein for the straight-through process for the preparation of compound of Formula I is performed in an organic solvent. There is no particular restriction on the nature of the organic solvent to be employed, provided that it has no adverse effect on the reaction or on the reagents involved. Examples of suitable solvents for the said purpose include aromatic hydrocarbons selected from the group comprising benzene, toluene, xylene, and mixtures thereof.

The solvent used in the rearrangement reaction is a polar solvent for example a nitrile solvent.

The sequence of reaction steps is illustrated herein below:

wherein n and m each are independently selected from 0, 1, 2, 3, 4, 5, 6, 7, 8 or 9 and the sum of n+m is at least 2, and the compounds of Formula I and II have substituents $R_1$, $R_2$, $R_3$ and $R_4$, where $R_1$, $R_2$, R3 and $R_4$ are independently of and selected from hydrogen, alkyl, alkenyl, alkynyl, cycloalkyl, cyclo alkenyl, aryl, aralkyl and aromatic or non aromatic heterocycle, or
R1, R2, R3 and R4 can be combined together to form a substituted or unsubstituted cycloalkyl or cycloaryl moiety, including bicyclic or heterocyclic moieties.

In another embodiment disclosed herein is a process for the preparation of laurolactam of Formula III comprising:

Preparation of oxime of cyclododecanone comprising contacting cyclododecanone of Formula IV with hydroxyl amine hydrochloride, zinc oxide and sodium carbonate with no solvent is heated at about 85° C. for about one and half hour resulting into in-situ formation of water and cyclododecanone oxime as an intermediate, which is neither isolated nor purified instead is further contacted with toluene as azeotropic solvent to remove the water at about 100° C. to 130° C. to obtain anhydrous cyclododecanone oxime.

The said anhydrous cyclododecanone oxime is then contacted with acetonitrile as rearrangement solvent and heated at about 80° C. resulting into rearrangement reaction catalyzed by zinc chloride formed in-situ during the preparation of oxime, to obtain substantially pure desired product laurolactam of Formula III.

The reaction sequence is represented herein below:

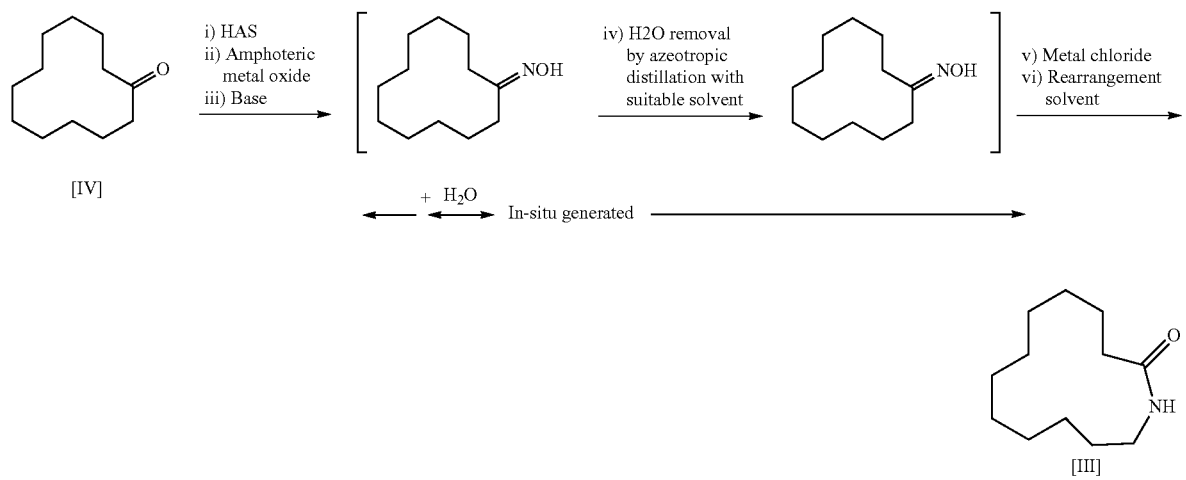

The following non limiting examples are provided to illustrate further the present invention. It will be apparent to those skilled in the art many modifications, alterations, variations to the present disclosure, both to materials, method and reaction conditions, may be practiced. All such modifications, alterations and variations are intended to be within the spirit and scope of the present inventions. It should be understood that the present invention is not construed as being limited thereto.

WORKING EXAMPLES

The present invention is further described according to the following working examples. The analysis is done by the gas chromatography.

Example 1: Preparation of Laurolactam 182 g (1 mol) cyclododecanone is charged into 1 lit flask equipped with thermo pocket, stirrer and contents and heated to melt at 80° C. followed by the addition of 76.4 g (1.1 mol) of hydroxyl amine hydrochloride and 8.14 g (0.1 mol) zinc oxide and 42.4 g (0.4 mol) sodium carbonate under stirring. Once the conversion of ketone reaches 90%, toluene is added to the reaction mass and temperature is raised to about 112° C. and the water formed is removed by azeotropic distillation in a Dean-Stark apparatus type distillation arrangement. The anhydrous cyclododecanone oxime is then mixed with acetonitrile and the reaction mass is heated at 80° C. till rearrangement reaction is complete. Acetonitrile is recovered and the desired laurolactam is then purified by crystallization from toluene. The yield of isolated laurolactam obtained is 175 g (96.1%, w/w w.r.t cyclododecanone) with 99.7% GC purity.

Example 2: Preparation of Laurolactam 182 g (1 mol) cyclododecanone is charged into 1 lit flask equipped with thermo pocket, stirrer and contents and heated to melt at 80° C. followed by the addition of 76.4 g (1.1 mol) of hydroxyl amine hydrochloride and 16.28 g (0.2 mol) zinc oxide and 31.8 g (0.3 mol) sodium carbonate under stirring. Once the conversion of ketone reaches 90%, toluene is added to the reaction mass and temperature is raised to about 112° C. and the water formed is removed by azeotropic distillation in a Dean-Stark apparatus type distillation arrangement. The anhydrous cyclododecanone oxime is then mixed with acetonitrile and the reaction mass is heated at 80° C. till rearrangement reaction is complete. Acetonitrile is recovered and the desired laurolactam is then purified by crystallization from toluene. The yield of isolated laurolactam obtained is 160 g (87.9%, w/w w.r.t cyclododecanone) with 99.7% GC purity.

Example 3: Preparation of Laurolactam 182 g (1 mol) cyclododecanone is charged into 1 lit flask equipped with thermo pocket, stirrer and contents and heated to melt at 80° C. followed by the addition of 83.3 g (1.2 mol) of hydroxyl amine hydrochloride and 8.14 g (0.2 mol) zinc oxide and 47.7 g (0.45 mol) sodium carbonate under stirring. Once the conversion of ketone reaches 90%, toluene is added to the reaction mass and temperature is raised to about 112° C. and the water formed is removed by azeotropic distillation in a Dean-Stark apparatus type distillation arrangement. The anhydrous cyclododecanone oxime is then mixed with acetonitrile and the reaction mass is heated at 80° C. till rearrangement reaction is complete. Acetonitrile is recovered and the desired laurolactam is then purified by crystallization from toluene. The yield of isolated laurolactam obtained is 171 g (94.0%, w/w w.r.t cyclododecanone) with 99.7% GC purity.

We claim:
1. A process for the preparation of cyclic amides of Formula I:

Formula I comprising the steps of
a) contacting a compound of Formula II

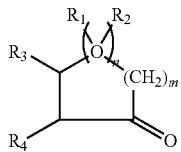

Formula II with a hydroxylammonium salt, amphoteric metal oxide and a base for in-situ preparation of corresponding compound of Formula X;

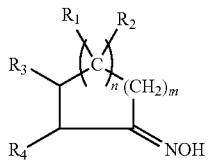

Formula X b) removing water formed; and
c) contacting the compound of Formula X with a rearrangement solvent and a metal salt formed insitu as a by-product during formation of the compound of Formula X to catalyse a rearrangement reaction resulting into formation of the cyclic amide Formula I;
wherein
$R_1$, $R_2$, $R_3$ and $R_4$ are hydrogen,
n is 1, and
m is 8.

2. The process of claim 1 wherein the water formed is removed by azeotropic distillation using a suitable solvent.

3. The process of claim 2 wherein the solvent is an aromatic hydrocarbon that comprises one of benzene, toluene, and xylene.

4. The process of claim 2 wherein the solvent is toluene.

5. The process of claim 1 wherein the hydroxylammonium salt is hydroxyl amine hydrochloride.

6. The process of claim 1 wherein the amphoteric metal oxide is zinc oxide.

7. The process of claim 1 wherein the base comprises an alkali metal oxide, an alkali metal hydroxide, an alkali metal carbonate, an alkali metal bicarbonate, or a mixture thereof.

8. The process of claim 1 wherein the base is sodium carbonate.

9. The process of claim 1 wherein the rearrangement solvent is a nitrile solvent.

10. The process of claim 1 wherein the rearrangement solvent is acetonitrile.

* * * * *